United States Patent [19]
Kain et al.

[11] Patent Number: 6,008,892
[45] Date of Patent: Dec. 28, 1999

[54] OPTICAL SUBSTRATE FOR ENHANCED DETECTABILITY OF FLUORESCENCE

[75] Inventors: Robert C. Kain, Cupertino; Eric G. Marason, San Francisco; Richard F. Johnston, Murphys, all of Calif.

[73] Assignee: Molecular Dynamics, Inc., Sunnyvale, Calif.

[21] Appl. No.: 08/864,363

[22] Filed: May 23, 1997

[51] Int. Cl.[6] ............................................. G01N 1/00
[52] U.S. Cl. ........................ 356/246; 356/317; 356/318
[58] Field of Search ................................ 356/246, 317, 356/318; 250/458.1; 436/524, 525, 527, 528

[56] References Cited

U.S. PATENT DOCUMENTS

| | | |
|---|---|---|
| 3,591,805 | 7/1971 | Schoeffel . |
| 3,604,927 | 9/1971 | Hirschfeld ............................ 250/483.1 |
| 4,877,965 | 10/1989 | Dandliker et al. .................... 250/458.1 |
| 5,091,653 | 2/1992 | Creager et al. ....................... 250/484.4 |
| 5,095,213 | 3/1992 | Strongin ............................... 250/459.1 |
| 5,394,268 | 2/1995 | Lanni et al. . |
| 5,414,508 | 5/1995 | Takahashi et al. ...................... 356/246 |
| 5,552,272 | 9/1996 | Bogart ..................................... 435/524 |
| 5,639,671 | 6/1997 | Bogart et al. ........................... 436/524 |

FOREIGN PATENT DOCUMENTS 43 01 005 A1   1/1993   Germany .

OTHER PUBLICATIONS

F. Jenkins et al., Fundamentals of Optics, Third Edition, publ. by McGraw–Hill Book Company, Inc., 1957, pp. 215–217 and 509–533.

Handbook of Optics, vol. II, 2nd Edition, publ. by McGraw–Hill, Inc., pp. 35.1–35.7 and 42.101–42.107, no date available.

Biostar STREP A O1A Package Insert, "An Enhanced Optical Immuno–assay for the Rapid Detection of Group A Streptococcal Antigen from Throat Swabs", pp. 1–12, no date available.

Biostar STREP B O1A Package Insert, "An Enhanced Optical Immuno–assay for the Rapid Detection of Group B Streptococcal Antigen from Cervical and Vaginal Swabs", pp. 1–13, no date available.

*Primary Examiner*—Robert H. Kim
*Attorney, Agent, or Firm*—Thomas Schneck; David M. Schneck

[57] ABSTRACT

A sample substrate for use in a fluorescence imaging system includes a rigid base with a specularly reflective surface, typically metal, on which is deposited a transparent coating layer. The coating layer has a thickness selected so that a particular fluorescence excitation wavelength, corresponding to a specified fluorescent constituent to be sought in sample material, has an optical path from the top of the coating layer to the reflecting surface in the base of substantially an odd multiple of one-quarter wavelength, so that the standing wave of the fluorescence excitation wavelength of light incident on the substrate has an antinode located at or near where sample material would be disposed on top of the coating layer. This maximizes fluorescence excitation of the sample on the reflective substrate. The transparent coating layer may be a dielectric material (e.g. silica) or may be a multilayer structure with a top layer of biologically active material for binding a specified sample constituent.

13 Claims, 2 Drawing Sheets

OPTICAL SUBSTRATE FOR ENHANCED DETECTABILITY OF FLUORESCENCE

TECHNICAL FIELD

The present invention relates to sample substrates, such as plates, slides and cells, for use in examining, indicating, analyzing or identifying fluorescent, phosphorescent or luminescent sample materials, e.g. tagged molecular biological specimens, and in particular relates to such sample holders whose optical structures are adapted for enhancing fluorescence detection and imaging.

BACKGROUND ART

Fluorescence microscopy is often used in the fields of molecular biology, biochemistry and other life sciences for analyzing biological molecules, including nucleic acids (DNA, RNA) and proteins (enzymes, antigens, etc.) that have been tagged or labeled with fluorescent probes. One such use is DNA diagnostics, such as for gene detection, in which a DNA sample is deposited on and bound to a glass substrate by means of a chemical binding agent, such as an aminosilane, present on the substrate surface, and a reagent, such as a carbodiimide vapor. The bound DNA on the substrate can then be imaged by fluorescence. The fluorescence of a sample was originally assessed by visual inspection through a conventional microscope, but this manual method has proved time-consuming and costly. Many different high-speed automated fluorescence imaging systems are now available.

An important figure of merit for fluorescence detection and measurement instruments is sensitivity, which is primarily determined by the signal-to-noise ratio (SNR) of the optical imaging system of the instrument. A well-designed imaging system has a signal-to-noise ratio that is limited by its light collection ability and not by internal noise sources. The theoretical SNR of such a system is expressed in terms of the number of photoelectrons at the cathode when using a photomultiplier tube (PMT), which in turn essentially depends upon the number of photons that reach the detector from the area of interest on the sample substrate, the quantum efficiency of the detector, and the number of dark electrons generated by the detector.

$$SNR = S/[S+2B]^{1/2},$$

where B is the total background noise and S is the measured signal less B. One obvious approach to increasing SNR, and thereby improving sensitivity, is to reduce background noise. Sources of background noise include specular or diffuse reflection of the fluorescence-stimulating laser light from the sample, autofluorescence of the substrate holding the sample, autofluorescence from the optics in the light path of the optical imaging system, stray light, and dark current of the detector. Stray light reaching the detector can be significantly reduced by proper size and placement of apertures in the imaging system. Both stray light and much of the reflected laser light can be rejected, while passing the fluorescent light, by using dichroic and other spectral filters and beamsplitters in the system. Autofluorescence of the optical elements can be reduced by avoiding use of lens cements in the light path, using glass instead of polymeric lenses, or using curved mirrors instead of lenses wherever possible. Autofluorescence of the substrate can be reduced by using low fluorescence materials, such as an ultrathin or opaque glass substrate. For example, in U.S. Pat. No. 5,095,213 Strongin discloses a plastic slide that is rendered opaque and substantially nonfluorescent with a quantity of black carbon powder in the plastic. Another way of handling autofluorescence is to use a pulsed or modulated excitation and to take advantage of the differences in emission decay rates between background fluorescence and specimen fluorescence, as disclosed in U.S. Pat. Nos. 4,877,965 to Dandiker et al. and 5,091,653 to Creager et al.

In U.S. Pat. No. 5,552,272, Bogart discloses an assay system and method for detecting the presence or amount of an analyte of interest. It includes a test substrate with an optically active surface that enhances the color contrast, i.e. differences in the observed wavelength (or combination of wavelengths) of light from the surface, between the presence and absence of the analyte in a sample applied onto the test substrate. In particular, the substrate may comprise a reflective solid optical support, such as a silicon wafer or metallic (e.g., aluminum) base, with an optical thin film coating thereon. The coating may comprise several layers, including for example an attachment layer on the upper surface of the support, and a receptive layer on the upper surface of the attachment layer containing a specific binding partner for the analyte of interest. The total coating thickness is selected to cause incident light to undergo thin film interference upon reflection, such that a specific color is produced. Specifically, the coating material(s) should have an overall thickness of a quarterwave of the unwanted color to be attenuated so that destructive interference of that color will occur. The substrate therefore has a particular background color, which can then be used as a comparative reference against a different observed color when an analyte of interest is present. Both qualitative visual inspection and quantitative instrumented measurement are suggested. Polarization contrast by means of an ellipsometer is also suggested.

One example of the use to which the Bogart invention has been put by Biostar, Inc. of Boulder, Colo., the assignee of the aforementioned patent, is an optical immunoassay (OIA) diagnostic screening test for the rapid detection (in under 30 minutes) of the presence of specific antigens of infectious pathogens n a sample taken from a patient. Commercial products include test kits for group A and group B streptococci and for chlamydia trachomatis. These particular assays are given as examples in the Bogart patent, are described in package inserts for the corresponding Biostar products and are also described in a number of published articles in medical journals. Briefly, they all rely on direct visual detection of a change in the color of light reflection off of the test substrate due to a physical change in the optical thickness of a molecular thin film coating on the substrate surface which results from binding reactions between an immobilized antibody on the test surface and a specific antigen that may be present in a drop of sample liquid applied to the test surface. The original bare test surface has a thin film thickness that results in a predominant visual background gold color when white light is reflected off of the surface. The antigen-antibody binding reaction that occurs when the specific antigen of interest is present in the applied sample results in an increase in the thin film thickness that causes a corresponding change in the color of the test surface from gold to purple. If on the other hand, the antigen is not present in the sample, no binding takes place, the original thin film thickness remains unchanged and the test surface retains its original gold color, indicating a negative result. This diagnostic assay tool is very sensitive and easily interpreted.

Bogart further discloses, in another embodiment of his invention (FIG. 17 of the aforementioned patent), the use of these substrates for enhanced fluorescence detection. After the analyte of interest has been bound to the surface by reaction with the specific binding partner in the receptive layer of the substrate coating, fluorescent label molecules may be attached to the analyte. In particular, the fluorescent molecules may be attached to any suitably selective and specific receptive material or reagent, such as a secondary antibody, and applied to the surface. The fluorescent labels are thus bound to the analyte of interest on the surface, if present, and immobilized to the surface through the analyte bridge. Directing light of an excitation wavelength onto the surface stimulates fluorescence of any of the label bound to the surface, thereby revealing the presence of the analyte of interest. Because the maximum fluorescence wavelength may not be shifted far enough from the excitation wavelength to be distinguished, the reflective substrate may have an antireflection layer whose thickness is selected to suppress reflection of the excitation wavelength, thereby reducing the background noise reaching the detector. Bogart states that the fluorescent signal generation is not dependent on the film thickness.

Even if the background noise is minimized (and even if the substrate is constructed so that the reflected or fluorescent sample signal stands out more clearly against the substrate's background by way of contrast), the maximum possible signal-to-noise ratio ($SNR_{max}$) is still limited to: $SNR_{max} = S^{1/2}$. Though the fluorescence signal S might be increased by increasing the output power of the laser, reflected laser noise will also increase, with possibly little improvement in the resulting SNR.

An object of the present invention is to provide an improved sample substrate which provides increased sample excitation and fluorescence emission.

DISCLOSURE OF THE INVENTION

The object has been met with a reflective sample substrate having a transparent coating layer thereon with controlled thickness that has been selected to ensure that a molecular sample placed on top of the coating layer is located at an antinode for the excitation light. In particular, the substrate includes a rigid base with a specularly reflective upper surface. The transparent coating on the upper surface of the base has a thickness selected such that for a particular excitation wavelength of light at normal incidence, the optical path from the top of the coating to the base reflecting surface is substantially an odd multiple (1, 3, 5, etc.) of one-quarter wavelength of the excitation light. The optical path length of the material is defined by the wavelength of light, the index of refraction of the material, and the angle of propagation through the material. Note also that the reflecting surface of the base is actually slightly below its physical surface by an amount equal to the sum of the skin (or penetration) depth of the reflective surface material and the optical depth of any surface oxidation on the base. A narrow excitation frequency linewidth is preferred.

The base can be made completely of metal or may be composed of a rigid bottom layer with a top metal coating. The metal can be aluminum, silver, gold or rhodium. The transparent coating may be a single layer of dielectric material, such as silica, alumina or a fluoride material (such as $MgF_2$). Alternatively, the transparent coating could be a multilayer coating with the top layer being a chemically reactive material for binding a specified biological sample constituent thereto.

By placing the sample on the coating layer at or near the antinode of the excitation light, maximum fluorescence excitation occurs. A reflective substrate also enhances fluorescence collection by nearly doubling the solid collection angle of a fluorescence imaging microscope system. Thus, the total fluorescence signal is increased, leading to a much improved signal-to-noise ratio. Also, because the coating layer is very thin, there is reduced fluorescence background noise from this material.

BEST MODE OF CARRYING OUT THE INVENTION

Figure 1:
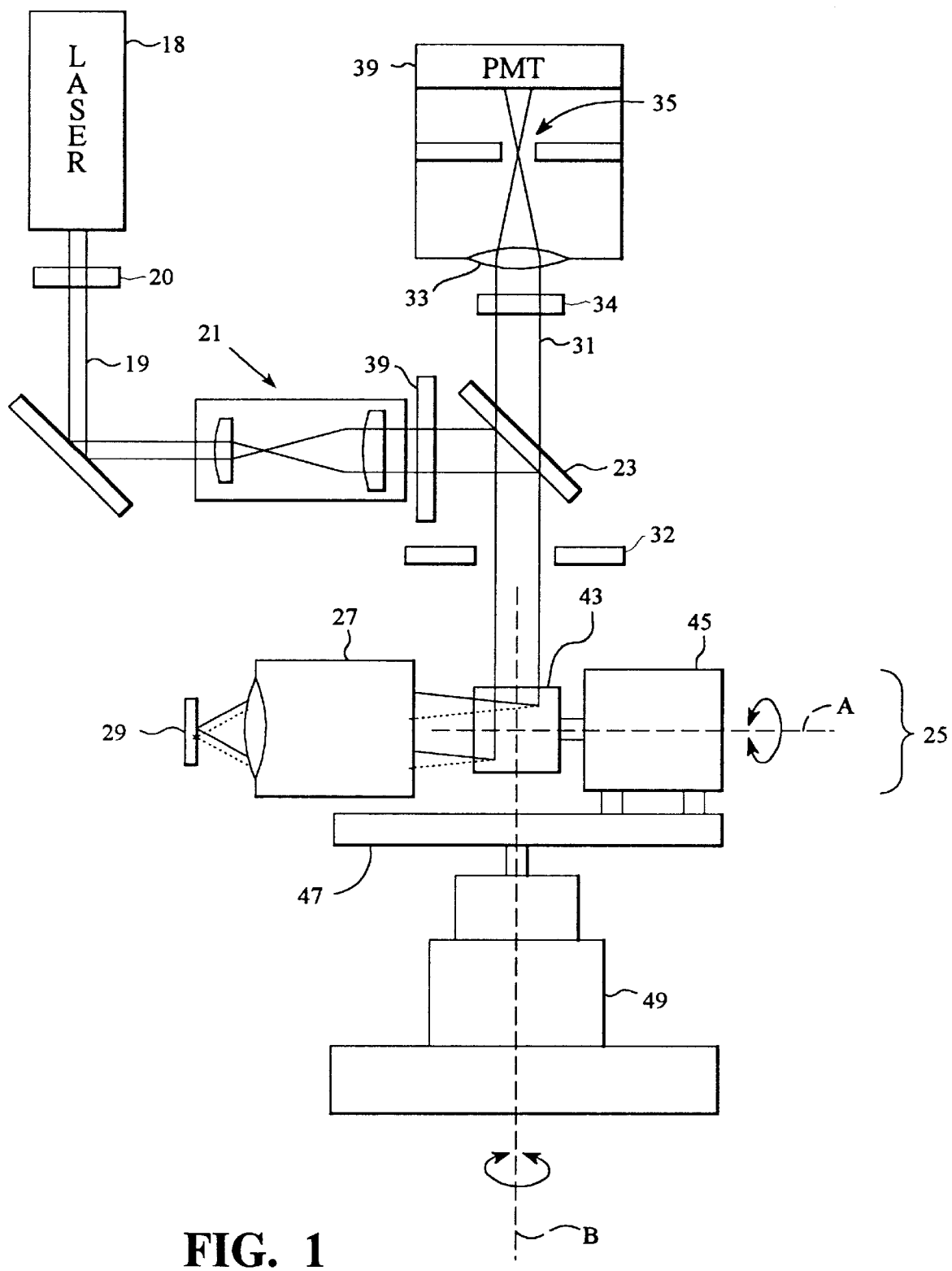
FIG. 1 is a schematic side plan of a fluorescence microscope system for use with the substrate of the present invention.

The sample substrate of the present invention can be used in any of a wide number of possible fluorescence microscope systems, including, for example, those described in U.S. Pat. Nos. 4,284,897 to Sawamura et al., 5,091,652 to Mathies et al., 5,296,700 to Kumagai, 5,381,224 to Dixon et al., and 5,504,336 to Noguchi, as well as U.S. patent application Ser. Nos. 08/595,355, 08/616,174 and 08/791,684, all assigned to the assignee of the present invention. One preferred fluorescence imaging system for use with the present invention is illustrated in FIG. 1.

A light source 18, such as a laser, produces a light beam 19. The beam is preferably a collimated beam of monochromatic coherent light. However, a noncoherent source, such as a light emitting diode (LED) could be used and a noncollimated source could be coupled to collimating optics to create a collimated beam. If the beam 19 is not monochromatic, it may be directed through a filter 20 to reduce any unwanted wavelengths.

The beam 19 is then directed through a beam expander 21 and reflected by a beamsplitter 23 onto a scanning device 25. Any scanning mechanism that produces a two-dimensional scan may be used. For example, the scanner 25 may have a first beam reflecting element 43, such as a galvanometer mirror or rotating polygon, pivotable or rotatable about a first axis A and moved by a motor 45, and a movable platform or turntable 47 rotated by a stepper motor 49 about a second axis B that is orthogonal to the first axis A, and upon which the first reflecting element 43 is supported. Reflector 43 need not have a planar reflecting surface, but could be concave or convex in one or both axes, or even have a diffracting surface.

The scanning beam is directed through an objective lens 27 to illuminate a spot, line or area on a sample 29. The objective 27 is preferably telecentric (or near telecentric) in the image plane so that the chief ray of the beam is always incident at substantially a right angle to the sample surface regardless of the scan position. With respect to the incident beam, the objective's focal plane should be proximate to the sample 29. The objective 27 provides coaxial illumination and collection. To maximize collection efficiency, it is preferred that the objective lens 27 have a large numerical aperture. The objective 27 preferably has an external pupil that coincides with the scan axes A and B at the reflective surface 43 so that collected light is directed as a retro-beam back toward the beamsplitter 23. The illuminating light beam 19 is an excitation beam that stimulates fluorescent light emission from the sample 29 at the illuminated spot. The fluorescent light is then collected by the objective lens 27, acting as a condenser, and directed as a retro-beam back along the incident light path (but in the opposite direction). Since the fluorescent light generally consists of a broad band of wavelengths different from the wavelength(s) of the incident stimulating beam, and since the system should be designed to work with a variety of fluorochromes, the system including the objective 27 is preferably largely achromatic and provides correction of chromatic aberrations over a range of wavelengths.

The retro-beam 31 may pass through an aperture or pupil of a spatial filter or stop 32 and through the beamsplitter 23. The beamsplitter 23 may act as a dichroic filter, reflecting the incident beam wavelength(s) and transmitting the fluorescent wavelengths (or vice versa), or can be any other type of beamsplitter capable of separating the light of the incident and retro-beams 19 and 31 (e.g., a polarization-sensitive beamsplitter in combination with a quarterwave plate). The retro-beam 31 may then be directed through a band-pass filter 34 and a focusing lens 33 onto limiting aperture 35. Light passing through the aperture 35 impinges upon a photodetector 39, such as a photomultiplier tube (PMT).

Whichever imaging system is used, it should preferably be capable of scanning at high speed over a large scan field with high resolution imaging and minimal optical aberrations. It should provide coaxial illumination and collection with high collection efficiency. An achromatic system with excellent color correction, as well as a system designed for minimizing background noise (including autofluorescence) is preferred.

Figure 2:
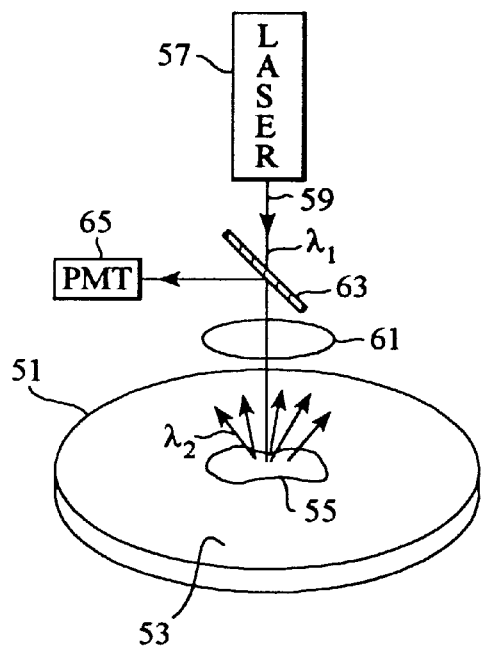
FIG. 2 is a general perspective view of a sample substrate of the present invention being used with a fluorescence imaging system like the microscope of FIG. 1.

With reference to FIG. 2, a sample substrate 51 of the present invention has on its upper surface 53 a fluorescent sample 55. The substrate 51 is designed to work with any fluorescence imaging system, like that shown in FIG. 1. Such a system is shown schematically in FIG. 2, with a laser light beam 57 providing a fluorescence-stimulating beam 59 of wavelength $\lambda_1$ that is directed through an objective 61 to the sample 55 on the surface 53. The sample 55 emits fluorescent light of wavelength $\lambda_2$, which is collected by the objective 61, separated from the incident light by a beamsplitter 63 and directed onto a PMT detector 65. The improved substrate 51 is constructed to maximize fluorescent emission and collection without having to increase the power of the laser beam 59 and without having to change the objective 61 or other optics in the system other than the substrate 51 itself.

Figure 3A:
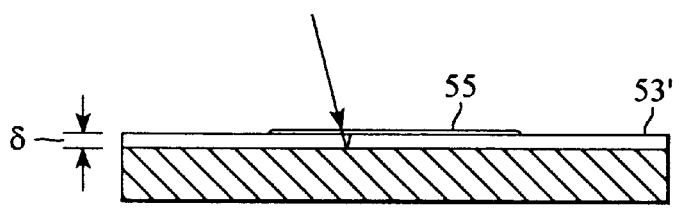
FIGS. 3A and 4A are close-up side section views of two sample substrates, one without a transparent coating (FIG. 3A) and the other, in accord with the present invention, having a transparent coating layer (FIG. 4A).

With reference to FIGS. 3A–3B and 4A–4B, the approach taken is to mirrorize the substrate onto which the fluorescent sample 55 is deposited. From the standpoint of geometric or "ray" optics, one might reason that such an approach should double the excitation by the incident light (because light rays would then illuminate the sample both directly and upon reflection) and should also double collection of the emitted fluorescence (because the fluorescent rays emitted away from the objective would be reflected back toward the objective, thereby effectively doubling the solid angle of collection). However, it has been discovered that this approach by itself does not work. If a bare reflective substrate 51' is used, as seen in FIG. 3A, then the sample 55 is actually found to experience only negligible excitation, and little, if any, fluorescence is observed, despite the fact that the reflectivity observed in the far field is increased as expected.

To understand this unexpected phenomenon we have to turn to a combination of physical optics and the wave theory of light. In 1890, O. Wiener reported his experiments showing standing waves produced by reflecting light at normal incidence from a polished mirror. By placing a thin photographic film at an incline to the mirror surface and then developing the exposed film, a system of separated dark bands on the film was produced. Decreasing the inclination angle caused the bands to move farther apart. The experiment was repeated two years later by P. Drude and W. Nernst using fluorescence to observe the phenomenon immediately without the need for photographic development. This phenomenon is understood to result from the superposition of incident and reflected light waves, producing standing waves with nodes and antinodes at different heights above the mirror surface. There is a node located at the reflecting surface (due to the finite conductivity of real metals, this is actually slightly below the physical surface) and the nodes are separated by a distance of one-half wavelength.

Figure 3B:
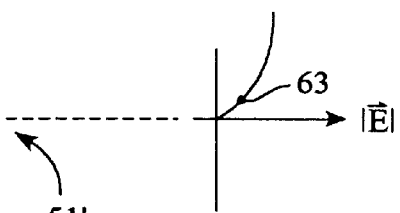
FIGS. 3B and 4B are graphs of electric field strength $|\vec{E}|$ versus depth for the substrates of FIGS. 3A and 4A, respectively, illustrating the advantage of the inventive substrate of FIG. 4A.

The problem that this phenomenon creates when attempting to produce fluorescence of a molecular sample on a bare mirror surface is that only negligible excitation occurs because the sample material is located near a node in the standing wave of the excitation light. As seen in FIG. 3A, a molecular sample 55 is located on top of the physical surface 53' of a bare metal substrate 51'. The reflective surface is slightly below the physical surface 53' by a distance 6 corresponding to the sum of the skin depth of the metal substrate 51' and the depth of ordinary surface oxidation. In the case of an aluminum substrate, the skin depth is about 13 nm thick and the surface oxide is about 2 to 5.5 nm thick, for a distance δ of about 16.5 nm. For 532 nm wavelength incident light, this distance δ amounts to about 4% of a wavelength. As seen in FIG. 3B, the field amplitude (for light, the electric field is the primary one of interest) is near zero at the location 63 of the molecular sample, since it is near a node of the standing wave set up by reflection. At best, the field amplitude seen by the sample would be only about 23% of the maximum amplitude at the location of an antinode. (The intensity, which goes as the square of the amplitude, is only 5% of maximum). The sample experiences little excitation, despite being located above a reflective surface, and produces very little fluorescence as a result.

Figure 4A:
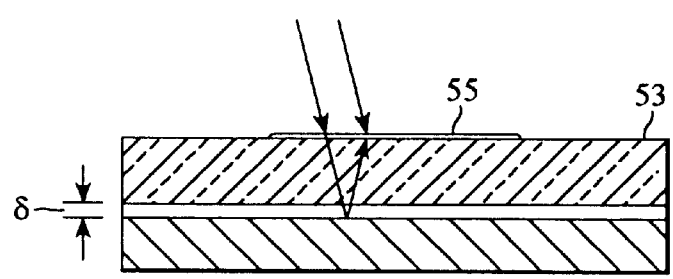

Referring now to FIG. 4A, the sample substrate 51 of the present invention solves this problem by recognizing that adding a transparent coating 53 of the proper thickness onto the reflective base can create a substrate 51 that locates a molecular sample at or near an antinode of the standing wave of the excitation light, thereby significantly increasing excitation and the resulting fluorescence emission. The coating 53 on substrate 51 should be such that the optical path length from the sample-coating interface to the skin depth within the reflective base is substantially equal to one-quarter wavelength.

In order to correctly determine the proper coating thickness, the incident angle of the excitation light and the refractive indices of the coating material and of the reflective base's surface oxidation must be taken into account. For normal incidence, the optical path length (OPL) is equal to the sum of the skin depth, the effective oxidation thickness and the effective coating thickness. For an aluminum base, the skin depth is about 13.1 nm. The aluminum oxide is about 3.5 nm thick and has a refractive index at 532 nm wavelength of about 1.772, for an effective optical thickness of about 6.2 nm. For 532 nm laser excitation light, a quarter wavelength is 133 nm. Thus, the coating must have an effective optical thickness of 114 nm. If we choose a silica coating 53, with a refractive index of 1.547 at 532 nm wavelength, we need a coating thickness of about 73.5 nm. If we use a different excitation source with a different wavelength of light, or a different reflective base or transparent coating material or a different incidence angle, the coating thickness will differ but should again be calculated to provide a one-quarter wavelength optical thickness (or odd multiples thereof).

Figure 4B:
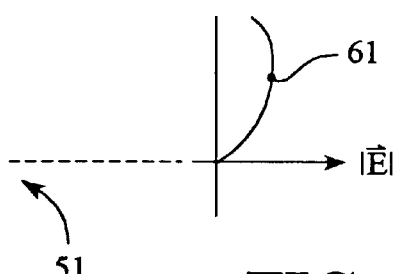

As seen in FIG. 4B, when the proper coating thickness is provided, the sample material 55 will be located at or near an antinode of the standing wave of the excitation light, i.e. near the position 61 where the electron field amplitude (and intensity) is at a peak. With maximum excitation, maximum fluorescence occurs. Even if the coating thickness is not exactly correct for the excitation wavelength, if the intensity is only 90% or 95% of the peak intensity, the fluorescence signal will still be significantly improved over prior sample substrates. Variations from the ideal thickness can occur due to uncertainties in skin depth, sample-to-sample variation in metal oxidation of the base prior to coating, and coating variations. Further, if two or more different wavelengths are to be used with the same substrate, a compromise thickness may be chosen that is adequate for all of those wavelengths, but possibly ideal for none. That is, the fluorescence imaging system of FIG. 1 could have one or more light sources providing multiple fluorescence excitation wavelengths, either simultaneously or selectably, for different fluorescent sample constituents, and the nominal optical thickness of the sample substrate can be selected to be approximately one-quarter wavelength (or an odd multiple) for each of the different excitation wavelengths. Further, the sample substrate could be mounted on a tiltable support to vary the tilt angle or orientation so as to select light incidence angle that allows the optical path to substantially match the quarter-wavelength condition for a selected one of the different wavelengths. When a different wavelength is selected, the substrate could be reoriented accordingly.

Base metals may include aluminum, silver, gold, rhodium, etc. It can even be a reflective coating layer on a glass slide or other rigid bottom layer. The transparent coating may be silica ($SiO_2$), alumina ($Al_2O_3$), magnesium fluoride ($MgF_2$) or some other dielectric material. It could also be multiple layers. The layer, or top layer, is not necessarily an inert material, but could be biologically active so as to bind with the sample material or a particular constituent of the sample.

What is claimed is:

1. A fluorescence imaging system, comprising
   a sample substrate for containing a fluorescent sample material on a top surface thereof,
   a light source providing light directed to said sample material on said sample substrate, said light including a fluorescence excitation wavelength particular to a specified fluorescent constituent of said sample material, and
   detection means for collecting and detecting fluorescent light emitted by said sample material containing said specified fluorescent constituent,
   wherein said sample substrate includes a rigid base with a generally flat, smooth, specular reflective surface, and a transparent coating layer deposited on said reflective surface of said base, said coating layer having a thickness selected such that an optical path from the top of said coating layer to the reflecting surface in said base is an odd multiple of one-quarter of said fluorescence excitation wavelength,
   whereby any sample material containing said specified fluorescent constituent and disposed on said top surface of said coating layer would be located near an antinode of a standing wave of said particular fluorescence excitation light wavelength incident on said substrate.

2. The system of claim 1 wherein said light source provides light directed at normal incidence onto said sample substrate.

3. The system of claim 1 wherein said optical path is substantially one-quarter wavelength of said light.

4. The substrate of claim 1 wherein said base is composed of metal.

5. The substrate of claim 1 wherein said base is composed of a rigid bottom layer with a top metal coating.

6. The substrate of claim 1 wherein said reflective surface is a metal selected from the group consisting of aluminum, silver, gold and rhodium.

7. The substrate of claim 1 wherein said reflective surface has a surface oxidation layer thereon.

8. The substrate of claim 1 wherein said coating layer is composed of a dielectric material.

9. The substrate of claim 8 wherein said coating layer is a dielectric selected from the group consisting of silica, alumina and a fluoride material.

10. The substrate of claim 8 wherein said coating layer includes multiple layers, the top layer of said multiple layers being chemically reactive for binding a specified biological sample constituent.

11. A method of imaging a sample material containing a specified fluorescent constituent, comprising
    disposing a sample material on a sample substrate,
    directing light including a fluorescence excitation wavelength particular to a specified fluorescent constituent into said sample material, said light thereby stimulating fluorescent emission by said sample material whenever said specified fluorescent constituent is present, and
    collecting and detecting any fluorescent light emitted from said sample material,
    wherein said sample substrate includes a rigid base with a generally flat, smooth, specular reflective surface, and a transparent coating layer deposited on said reflective surface of said base, said coating layer having a thickness selected such that an optical path from the top of said coating layer to the reflecting surface in said base is an odd multiple of one-quarter of said fluorescence excitation wavelength,
    whereby any sample material containing said specified fluorescent constituent and disposed on said top surface of said coating layer would be located near an antinode of a standing wave of said particular fluorescence excitation light wavelength incident on said substrate.

12. A fluorescence imaging system, comprising
    a sample substrate for containing a fluorescent sample material on a top surface thereof,
    at least one light source providing light directed to said sample material on said sample substrate, said light from each said light source including a fluorescence excitation wavelength particular to a specified fluorescent constituent of said sample material, such that different wavelengths of light can excite fluorescence from different constituents in said sample material, and
    detection means for collecting and detecting fluorescent light emitted by said sample material containing a plurality of different fluorescent constituents of said sample material,
    wherein said sample substrate includes a rigid base with a generally smooth, specular reflective surface, and a transparent coating layer deposited on said reflective surface of said base, said coating layer having a thickness selected such that an optical path from the top of said coating layer to the reflecting surface of said base is approximately an odd multiple of one-quarter wavelength for light of each fluorescence excitation wavelength from said at least one light source.

13. The system of claim 12 further including sample substrate support and excitation means for tilting said sample substrate to vary an angle of incidence of light from said at least one light source, such that for each selected fluorescence excitation wavelength, a tilt angle of said substrate is also selected so that said optical path is substantially equal to an odd multiple of one-quarter of that selected wavelength.

* * * * *